(12) United States Patent
Danley

(10) Patent No.: US 8,066,429 B2
(45) Date of Patent: Nov. 29, 2011

(54) SYSTEM AND METHOD FOR THERMAL ANALYSIS USING VARIABLE THERMAL RESISTANCE

(75) Inventor: Robert L. Danley, Collingswood, NJ (US)

(73) Assignee: Waters Technologies Corporation, Milford, MA (US)

( * ) Notice: Subject to any disclaimer, the term of this patent is extended or adjusted under 35 U.S.C. 154(b) by 482 days.

(21) Appl. No.: 12/130,553

(22) Filed: May 30, 2008

(65) Prior Publication Data

US 2008/0304540 A1 Dec. 11, 2008

Related U.S. Application Data

(60) Provisional application No. 60/942,242, filed on Jun. 6, 2007, provisional application No. 60/942,245, filed on Jun. 6, 2007.

(51) Int. Cl.
*G01K 7/00* (2006.01)
*G01N 25/00* (2006.01)
(52) U.S. Cl. ............. 374/31; 374/43; 374/141; 374/10; 374/12
(58) Field of Classification Search ............ 374/141, 374/120, 31, 10, 12, 43
See application file for complete search history.

(56) References Cited

U.S. PATENT DOCUMENTS

| | | | |
|---|---|---|---|
| 2,769,334 A | 11/1956 | Soehngen | |
| 3,491,581 A | 1/1970 | Roberts et al. | |
| 4,095,453 A | 6/1978 | Woo | |
| 4,117,050 A | 9/1978 | Appel et al. | |
| 4,429,684 A | 2/1984 | Greiner | |
| 4,850,713 A | 7/1989 | Thery et al. | |
| 5,363,391 A | 11/1994 | Matthews et al. | |
| 5,484,204 A | 1/1996 | Danley | |
| 5,509,733 A | 4/1996 | Danley | |
| 5,655,681 A | 8/1997 | Vogel et al. | |
| 6,403,925 B1 | 6/2002 | Johnsgard et al. | |
| 6,431,747 B1 | 8/2002 | Danley | |
| 6,488,406 B2 | 12/2002 | Danley | |
| 6,488,408 B1 | 12/2002 | Laflamme et al. | |
| 6,491,425 B1 | 12/2002 | Hammiche et al. | |
| 6,523,998 B1 | 2/2003 | Danley et al. | |
| 6,561,692 B2 | 5/2003 | Danley | |
| 6,578,367 B1 | 6/2003 | Schaefer et al. | |
| 6,648,504 B2 | 11/2003 | Danley | |
| 6,843,595 B2 | 1/2005 | Danley | |
| 7,025,497 B2 | 4/2006 | Danley | |
| 2002/0015801 A1 | 2/2002 | Emch | |

(Continued)

OTHER PUBLICATIONS

International Search Report Dated Sep. 16, 2008.
U.S. Appl. No. 12/129,355, filed May 29, 2008.
United Kingdom Patent Application No. GB0919874.8, Examination Report, Mailing Date: Mar. 1, 2011, 7 pages.
United Kingdom Patent Application No. GB0919874.8, Examination Report, Mailing Date: May 6, 2011, 1 page.

(Continued)

*Primary Examiner* — Lisa M Caputo
*Assistant Examiner* — Mirellys Jagan

(57) ABSTRACT

A thermal measurement apparatus and method for performing heat flux differential scanning calorimetry (DSC) is disclosed. A variable thermal resistor is used to couple a measurement assembly to a heat sink in the thermal measurement apparatus, such that samples can be rapidly heated and rapidly cooled. The apparatus can be configured with a highly conductive sample assembly enclosure. The enclosure can include a high emissivity coating. In one embodiment, the enclosure extends along a longitudinal direction that is about the same as that of an infrared lamp assembly used to heat the enclosure, thereby increasing the efficiency of heating the sample enclosure. In one configuration, the variable thermal resistor comprises a gap whose gas composition can be varied during a sample measurement to independently optimize sample heating and cooling rates.

35 Claims, 11 Drawing Sheets

U.S. PATENT DOCUMENTS

| | | |
|---|---|---|
| 2003/0026319 A1 | 2/2003 | Kinoshita |
| 2003/0101612 A1 | 6/2003 | Granneman et al. |
| 2003/0142721 A1 | 7/2003 | Hammer et al. |
| 2003/0165179 A1 | 9/2003 | Danley |
| 2006/0140246 A1 | 6/2006 | Danley et al. |
| 2006/0187998 A1 * | 8/2006 | Danley .......................... 374/10 |

OTHER PUBLICATIONS

United Kingdom Patent Application No. GB0919874.8, Notification of Grant, Mailing Date: Jul. 19, 2011, 2 pages.

United Kingdom Patent Application No. GB1110397.5, Examination Report, Mailing Date: Jul. 13, 2011, 4 pages.

* cited by examiner

SYSTEM AND METHOD FOR THERMAL ANALYSIS USING VARIABLE THERMAL RESISTANCE

This application claims the benefit of U.S. Provisional Application Nos. 60/942,242 filed Jun. 6, 2007 and 60/942,245 filed on Jun. 6, 2007, which are herein incorporated by reference in their entirety.

BACKGROUND

Field of the Invention

The present invention relates generally to apparatus and methods for materials property measurements performed during heating and cooling.

Differential thermal analysis (DTA) and differential scanning calorimetry (DSC) can be performed at high sample heating rates, as described in U.S. Pat. No. 5,509,733 to Danley ("the '733 patent"), which discloses an "Infrared Heated Differential Thermal Analyzer" that allows both rapid heating and rapid cooling rates to be achieved. The '733 patent discloses the use of an infrared heat source to heat a differential thermal analysis (or potentially a differential scanning calorimetry) measuring assembly that is coupled to one or two heat sinks via one or two heat flow restricting elements that limit the rate of heat flowing between the heat sink and the measuring assembly. The heat sinks are cooled by either circulating a cold fluid through them or by supplying a sub-cooled liquid that evaporates within the heat sink carrying away heat. The sub-cooled liquid may be the refrigerant in a vapor compression refrigeration system or it may be an expendable coolant such as liquid nitrogen whose vapor is discharged to the atmosphere after cooling the heat sink.

The furnace disclosed in the '733 patent can be used in conjunction with a measuring assembly that comprises a disk-type sensor constructed according to U.S. Pat. No. 4,095,453, where the sensor is joined to a pair of high thermal conductivity metal temperature-equalizing rings, one ring joined to each side of the sensor disk. The rings are joined to the heat restricting elements (also termed "thermal resistors" herein), which are in turn joined to the heat sinks. The heat restricting elements are thin-walled cylinders made of relatively low thermal conductivity metals that are resistant to high temperatures and the large thermal stresses that may be imposed upon them. In the case of an apparatus having a single heat sink, the heat restricting element is joined to the temperature-equalizing ring located beneath the sensor and a second thin-walled section similar to the heat restricting element is joined to the upper temperature-equalizing ring. Use of a high thermal resistance heat restricting element can facilitate high sample heating rates by reducing unwanted heat dissipation from the sensor during heating.

Although the apparatus disclosed in the '733 patent can achieve relatively high heating rates and cooling rates, the apparatus cooling rate is nevertheless limited by such factors as the temperature of the heat sink (the lower the heat sink temperature, the higher the cooling rate from an elevated temperature), which in turn depends on the temperature of the coolant and the geometry of the heat sink. In addition, the cooling rate is limited by the thermal resistance of the heat restrictor elements which tend to limit the rate of heat dissipation from the sensor during cooling.

Furthermore, the apparatus described in the '733 patent is not well suited to perform differential scanning calorimetry because the sensor and the sample containers exchange heat with the heat restricting elements, the heat sinks and the measuring assembly cover in the case of the thermal analyzer having a single heat sink. Given that the temperature differences between the sensor and the heat sinks and between the sensor and portions of the heat restricting elements is often of the order of several hundred degrees, and may even reach 1000° C. or more, the heat exchange may be quite large. Since this heat does not flow through the sensor, it is not measured; thus the unmeasured heat exchange constitutes a heat flow rate measurement error. For some experiments where quantitative heat flow rate measurement is not necessary, for instance experiments where only the temperature of a transition is measured, and only knowledge of the direction of the heat exchange, i.e. whether the transition is exothermic or endothermic, is required, the apparatus of the '733 patent may be adequate.

On the other hand, a conventional heat flux DSC can be constructed by installing a sensor within a uniform temperature enclosure that is heated and cooled according to the desired experimental temperature program. This greatly reduces the temperature differences between the sensor and sample containers and their surroundings, thereby reducing the unmeasured heat exchange between sensor and sample containers and the enclosure. However, such enclosures generally have relatively high heat capacities and thus are not well suited to heating and cooling at high rates. Moreover, the enclosures are typically heated by resistance heating elements that must be electrically and thermally insulated from the DSC enclosure. Thus, the heating elements do not transfer heat rapidly to the DSC enclosure and when power is removed they cool slowly. The heating elements and electrical and thermal insulation of the heating elements also add mass to the USC, increasing its heat capacity, further limiting its ability to heat and cool rapidly.

Thus, many obstacles exist to achieving a system for rapid sample heating and rapid sample cooling that is compatible with thermal analysis of samples, such as heat flux DSC.

BRIEF SUMMARY OF THE INVENTION

In one configuration of the present invention, a thermal measurement system comprises a measurement assembly having a differential thermal analysis sensor assembly for receiving a sample that is installed in a cavity within an elongated cylinder, an infrared lamp assembly disposed circumferentially around the elongated cylinder and having a length substantially similar to that of the cylinder. The infrared lamp assembly preferably comprises a plurality of tubular lamps each having a longitudinal axis arranged parallel to the axis of the elongated cylinder, and an infrared reflector comprising a plurality of partial quadric cylindrical surfaces that each describe a cylindrical shape that has a focus coincident with the axis of each tubular lamp. The thermal measurement system further comprises a thermal resistor coupled to the measurement assembly, wherein the thermal resistor has a configurable thermal resistance, whose perimeter is defined by the lamp assembly, and a heat sink thermally coupled to the thermal resistor and to the infrared reflector, wherein the thermal resistor is operable to dynamically vary the thermal resistance between the measurement assembly and the heat sink at appropriate moments during an experiment.

In another embodiment of the present invention, a method for performing thermal measurement comprises providing a variable thermal resistor between a sample measurement assembly and a heat sink in a thermal analysis instrument, heating a sample in the sample measurement assembly when the variable resistor has a first thermal resistance, altering the variable resistor so that the variable resistor has a second thermal resistance different from the first thermal resistance, and cooling the measurement sample while the variable resistor has the second thermal resistance, wherein the sample heating and cooling rates are configured to vary independently.

BRIEF DESCRIPTION OF THE DRAWINGS

FIG. 2 shows a horizontal cross sectional view through the infrared furnace and measuring assemblies depicted in FIG. 1a.

DETAILED DESCRIPTION OF EMBODIMENTS

Figure 1A:
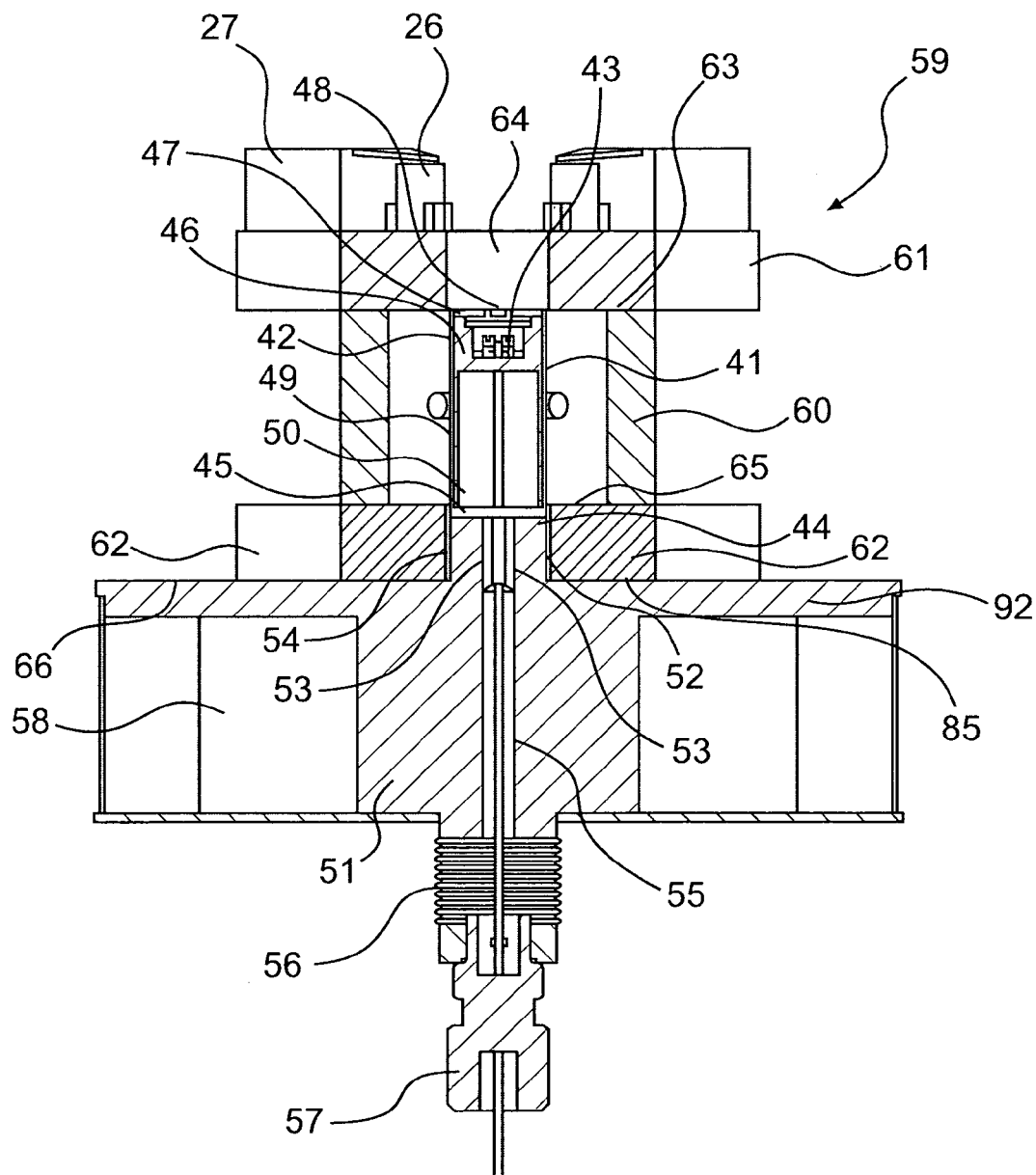
FIG. 1a is a schematic diagram that shows a vertical cross section through the centerline of a calorimeter measuring assembly according to one configuration of the present invention.

In order to clarify the present invention, embodiments of the present invention are discussed below with respect to FIGS. 1-5.

In one configuration of the present invention, a system for thermal measurement includes an infrared furnace used to heat a measuring assembly that incorporates a high thermal conductivity enclosure similar to that of a conventional DSC. The terms "system for thermal analysis," "thermal measurement system, and "thermal analysis system" are used interchangeably herein to denote generally a system that is configured to measure the thermal properties of a sample, including DTA and DSC and related techniques. The enclosure reduces temperature difference errors that result from heat exchange between the sensor, sample containers and their surroundings.

In configurations of the present invention described in detail below, the exterior surface of the enclosure that houses the measurement assembly is an elongated circular cylinder that is equal in length to a reflector cavity and lamp assembly that forms an infrared heating assembly. In this manner, the enclosure intercepts a significant fraction of the energy emitted by the lamps and reflected by the reflector. The enclosure exterior surface is coated with a high emissivity coating to greatly increase the absorption of radiation arriving at the surface. Accordingly, by ensuring that the enclosure geometry is configured to intercept and absorb a larger fraction of the emitted radiation, even a relatively massive enclosure can be heated rapidly.

In addition, in embodiments of the present invention, the ratio of heated area to reflector area is increased compared to a system having a quartz tube enclosing the measuring assembly, such as that depicted in the '733 patent. Elimination of a quartz enclosure further improves heat exchange efficiency and allows the lamps to be positioned closer to the measuring assembly, which, in turn, allows the reflector surface area to be reduced.

Preferably, a single heat sink is located externally to the infrared furnace reflector, so that the heat sink is not directly heated by radiation, which further improves the efficiency of infrared heating. The heat sink may be cooled by circulating water or some other fluid as a coolant. Alternatively, the heat sink may be cooled by evaporation of a sub-cooled liquid, which may be the refrigerant in a vapor compression refrigeration system, or an expendable coolant such as liquid nitrogen whose vapor is discharged to the atmosphere.

In addition, the system includes a thermal resistor used to provide a heat flow path ("thermally connect") the measuring assembly to the external heat sink, where the thermal resistor is also located externally to the reflector. The purpose of the thermal resistor is to limit the rate of flow of heat between the measurement assembly and the heat sink but to also allow sufficient heat to flow that the measurement assembly may be cooled at the desired rate. Thus, the requirements for the thermal resistor are generally different for heating, when a large thermal resistance is often desired than for cooling, when a small thermal resistance is generally desired. The thermal resistor comprises a gas-filled gap whose gas composition can be configured to modify the thermal resistance of the thermal resistor. Preferably, the thermal resistor is also located externally to the reflector, wherein the resistor is disposed outside the region defined by the reflector cavity.

In configurations of the present invention, the diameter of the enclosure and measurement assembly can be conveniently scaled to small dimensions, such that the mass of the measurement assembly and enclosure are much less than in a typical DSC apparatus. This further facilitates the ability to rapidly heat and cool a sample during sample measurements.

Rather than using a separate cooling system for the reflector as described in the prior art, in configurations of the present invention, the reflector is also thermally coupled to the heat sink for cooling. In this manner, the cooling rates and the minimum temperature achieved by the apparatus are improved. This configuration has the further advantage that the apparatus is simplified by elimination of a separate cooling system for the infrared reflector.

FIG. 1a shows a vertical cross section through a thermal measurement system having an assembly in which a gas-filled gap thermal resistor is used to couple the measuring assembly to a heat sink. To enhance the heating and cooling rates attainable, the measuring assembly is greatly reduced in size compared with conventional measuring assemblies, as are those of the sample and sample containers employed. Measuring assembly 41 comprises high thermal conductivity enclosure 42, sensor assembly 43 and thermal resistor 44.

In addition to having high thermal conductivity, enclosure 42 preferably exhibits high emissivity on its outer surface. In embodiments of the present invention these two properties can be achieved in more than one manner. Enclosure 42 can comprise a cylinder that contains a single material than has high thermal conductivity and high emissivity, such that the outer surface of enclosure 42 also has high emissivity. Alternatively, enclosure 42 can comprise a cylinder having a given cylinder wall thickness, whose inner portion is made of a highly thermally conductive material that does not have high emissivity. In the latter case, an outer layer of the cylinder wall, which may comprise an outer coating applied to the cylinder, has high emissivity, such that the outer surface of the cylinder exhibits high emissivity. In both cases, the overall thermal conductivity of the enclosure remains high.

In one embodiment of the present invention, high thermal conductivity enclosure 42 is made of commercially pure silver, and is arranged in the shape of a cylinder, preferably a cylinder having circular cross-section ("circular cylinder"), that includes cavity 46, which is closed by inner lid 47 and outer lid 48, each also made of silver. Cylindrical outer surface 49 is coated with a high emissivity coating that enhances the infrared absorbtivity of the surface. One such suitable coating is LaserBlack, a proprietary coating produced by Epner Technology Inc. of Brooklyn, N.Y. In one configuration of the present invention, heat flux differential scanning calorimeter sensor assembly 43 as described in U.S. Pat. No. 6,431,747 and in U.S. patent application Ser. No. 11/843,225, filed Aug. 22, 2007 (which is based on U.S. Patent Application No. 60/839,673, filed Aug. 24, 2006), is inseparably joined to the base of cavity 46 of enclosure 42 by brazing, which ensures that the heat exchange between the sensor and the enclosure is highly repeatable. In embodiments of the present invention, the heating efficiency of the measurement assembly can exceed 50%.

Because the sample and sample container sizes in the embodiment depicted in FIG. 1a are very small, the sensor assembly 43 is preferably fitted with cylindrical cavities on both the sample and reference positions, which aid in placing and holding the sample containers, as further discussed with respect to FIG. 3 below. Further, the cylindrical cavities reduce the thermal contact resistance between the sample capsules and the sensor by increasing the surface area for heat exchange. The reduced thermal resistance aids in reducing temperature lag between sample capsule and sensor that can occur when high heating and cooling rates are employed.

Figure 1B:
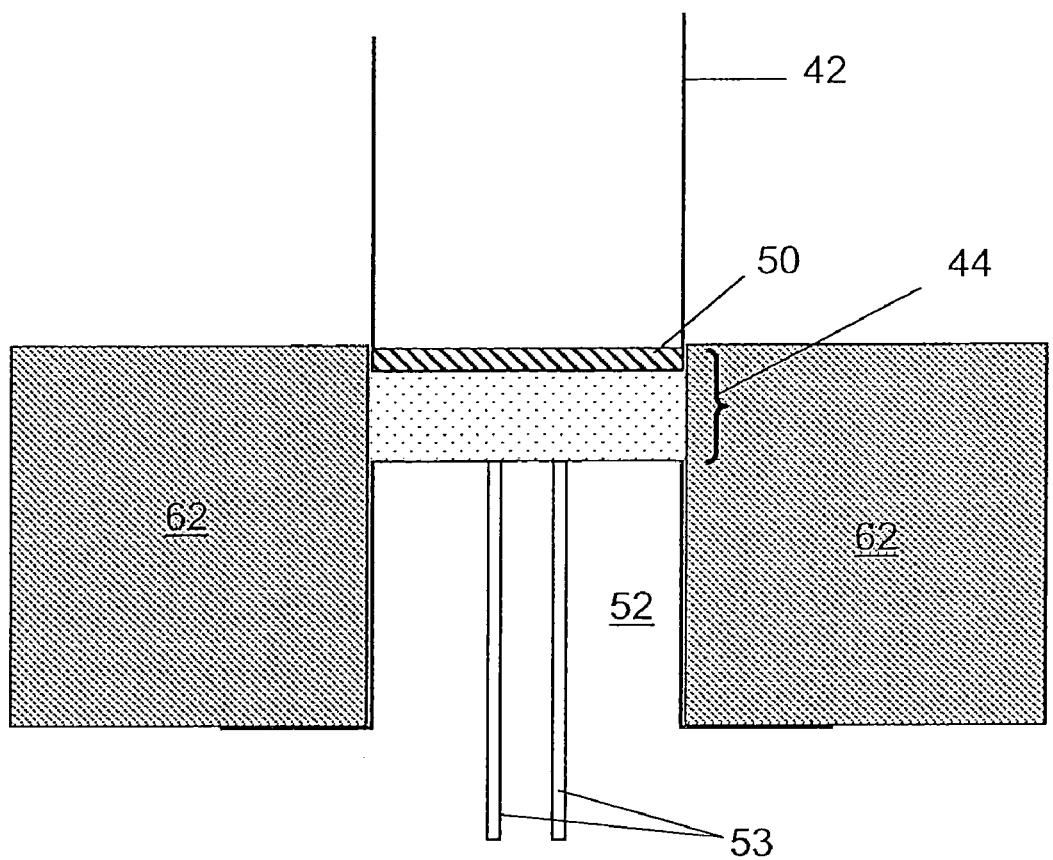
FIG. 1b depicts details of a thermal resistor having variable thermal resistance according to one configuration of the present invention.
Figure 1C:
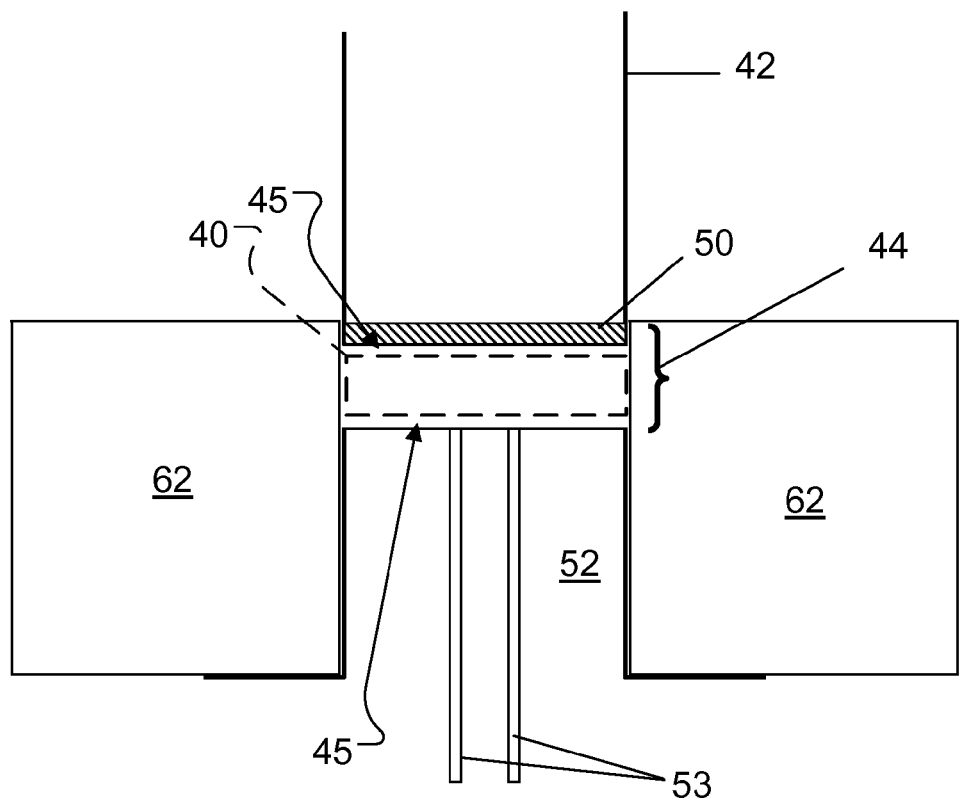
FIG. 1c depicts details of a thermal resistor having variable thermal resistance including one or more thin spacers.

A flat silver plate 50 that is an integral part of the measuring assembly forms one surface of a gas-filled gap thermal resistor 44, as depicted in FIG. 1b.

Gas-filled gap 45 is disposed between plate 50 and the opposite surface of thermal resistor 44 formed by heat sink extension 52, which extends upwards into the reflector bottom plate 62 to support the measuring assembly.

In accordance with one embodiment of the present invention, gas-filled gap 45 is a simple gap that results when two nominally flat surfaces are pressed together. For example, heat sink 51, which comprises outer portion 92 and heat sink extension 52 disposed in the center of heat sink 51, can be configured such that heat sink extension 52 comes into nominal contact with plate 50 when heat sink 51 is assembled to measurement assembly 41. In such a configuration, the resulting gas-filled gap occurs because the two nominally flat surfaces—plate 50 and the top of heat sink extension 52—are not perfectly flat, so that gas fills spaces between the nominally flat surfaces. The average vertical dimension of the resulting gas-filled gap corresponds to the average vertical separation between the top of heat sink extension 52 and the bottom of plate 50 taken over the planar area between heat sink extension 52 and plate 50. Thus, because neither the surface of heat sink extension 52 or that of plate 50 may be ideally flat, that is, each surface has some degree of roughness or non-planarity, when plate 50 and heat sink extension 52 are brought into contact, there will be many gaps between the actual points of contact between plate 50 and heat sink extension 52, which can be expressed as an average vertical gap.

In another embodiment of the present invention, as depicted in FIGS. 1a and 1b, the heat sink extension 52 can be configured such that a finite vertical gap 45 exists between plate 50 and the top of heat sink extension 52 (that is, there is no contact between plate 50 and heat sink extension 52), when surface 66 is assembled against bottom plate 62.

Exemplary dimensions of gas-filled gap 45 include a lateral width (diameter) ranging from a few millimeters to several centimeters, corresponding to the diameter of heat sink extension 52, and a vertical dimension ranging from a few tenths of a millimeter down to nominally zero millimeters, as discussed above. However the present invention is not limited to any particular size range of gas-filled gap 45, nor is the invention limited to a particular vertical-to-horizontal ratio of gas-filled gap 45.

Referring again to FIG. 1a, two small diameter passages 53 that extend through the heat sink extension supply gas to thermal resistor 44; passages 53 are supplied by a larger passage 55 that passes through the heat sink where it is closed by a bellows 56 and a seal arrangement 57 to which the gas source is connected. In accordance with another embodiment of the present invention, the bellows also performs the additional function of holding the measuring assembly in place and maintaining the vertical height of gap 45 of the thermal resistor. When the measuring assembly is installed to heat sink 51, it is held in place against heat sink extension 52 and bellows 56 is compressed. Seal arrangement 57 is configured to be tightened, clamping the seal arrangement to the thermocouple protection tubes and thereby exerting a force that holds bottom plate 50 of the measuring assembly firmly in place against heat sink extension 52. Tightening of seal arrangement 57 tends to pull plate 50, which is coupled to thermocouple protection tubes that pass through passage 55, towards heat sink extension 52. Accordingly, the tightening process can be used to maintain plate 50 in contact with heat sink extension 52.

In another embodiment of the present invention, thin spacers 40 (FIG. 1c) are disposed within gas-filled gap 45 to increase the effective thermal resistance. In one embodiment of the present invention, the spacers are thin metal sheets that extend horizontally across the diameter of gas-filled gap 45. For example, the thin metal sheets can have be circular disks having a diameter that ranges in size up to that of gas-filled gap 45. Thus, the thin spacers are disposed in a layer-like fashion within gas-filled gap 45.

In accordance with embodiments of the present invention, even though thin sheets of metal typically have inherently low thermal resistance because they are thin and are made of relatively high thermal conductivity material, the thermal resistance of gas-filled gap 45 is increased when the thin sheets are horizontally disposed within the gap. This is because the presence of one or more horizontal thin metal sheets increases the thermal resistance by increasing the number of thin gas layers within the interface between plate 50 and extension 52. Without any thin horizontal metal sheet spacer ("spacer") within gap 45, there is only a single gas layer between plate 50 and extension 52, such as the configuration depicted in FIG. 1b. Addition of one spacer increases the number of gas layers to two: one gas layer lies between the spacer and plate 50, and one gas layer lies between the spacer and extension 52.

Because the top and bottom surfaces of each spacer retains a degree of non-planarity or roughness, many gaps persist between adjacent spacers even when they are brought into contact with each other, producing an effective gas layer between adjacent spacers. Accordingly, insertion of each additional spacer within gap 45 increases by one the number of gas layers, thereby increasing the thermal resistance of the gap assembly for any given gas composition. In one embodiment of the present invention, two spacers are disposed within gap 45, providing three gas layers within the gap.

Exemplary spacer thickness can be about 0.0005" to about 0.01," which thickness range is suitable to produce small gas-filled gaps 45 as described below.

In accordance with an embodiment of the present invention, one or more thin spacers 40 (FIG. 1c) are placed horizontally in a spacer stack (that is, the spacers are arranged in layer-like fashion) between heat sink extension 52 and plate 50, after which seal arrangement 57 is tightened such that the spacer stack comes into nominal contact with both heat sink extension 52 and plate 50. In one embodiment of the present invention, the total average vertical gap spacing, which is the sum of the average vertical gaps created between any spacers in the stack, the average gap between the top of the spacer stack and plate 50, and the average gap between the bottom of the spacer stack and heat sink extension 52, is about 0.0001"-0.002." By selecting the appropriate number of spacers, together with the appropriate surface roughness, among other parameters, the total average vertical gap can be engineered to a achieve a desired dimension, to provide for a desired range of achievable thermal resistance.

The user of thin spacers provides multiple advantages for engineering thermal resistance in assembly 59. For example, if a user desires a range of thermal resistance that requires an average vertical gap to be about 0.001," in order to try to achieve the vertical separation the top of extension 52 could be brought into approximately 0.001" proximity to plate 50. However, it can be exceedingly difficult to reproducibly achieve such a small gap, for example, by adjusting seal arrangement 57, let alone to determine when the appropriate gap is achieved. In contrast, the use of thin spacers facilitates more accurate control of a vertical gap by allowing a user to assemble heat sink extension 52 and plate 50 together until contact is made on both top and bottom surfaces of the interposed thin spacer stack, at which point a tight fit is achieved in which each spacer is in contact with an external surface on the top side and bottom side. Because the surface roughness of the top of heat sink extension 52 and bottom of plate 50, as well as that of the interposed spacers, tends to persist, substantially the same effective gap can be produced each time heat sink extension 52 is tightened against plate 50. In this manner, a user could determine by trial the number of spacers needed to produce the desired gap dimension or the desired thermal resistance range.

Moreover, by varying the composition of the gas supplied to the gap in thermal resistor 44, the thermal resistance, and hence the rate of heat flow between the measuring assembly and the heat sink, may be varied. Variation of the heat flow rate, in turn, changes the heating and cooling rates that may be obtained. For example, if a low conductivity gas such as argon (or a vacuum, in configurations where the gap is designed to support a vacuum) is used, the relative heating rate can be increased, while the relative cooling rate is decreased. If a high thermal conductivity gas composition is used instead, the relative heating rate is decreased, but the relative cooling rate is increased. Accordingly, the gas composition in thermal resistor 44 can be configured (tailored) to vary maximum sample heating and cooling rates according to experimental needs. In one embodiment of the present invention, a thermal resistor is configured to produce a thermal resistance when He is used to fill the gas gap that is several times lower than the thermal resistance when $N_2$ is used to fill the gas gap.

Coolant is supplied to cavity 58 in the heat sink where the coolant contacts surfaces of the heat sink to extract heat. Fins may be added to increase the area of the heat sink surface if needed according to the magnitude of heat exchange. If the coolant is liquid nitrogen, the flow rate of liquid nitrogen may be controlled using the apparatus and the method disclosed in U.S. Pat. No. 6,578,367 to Schaefer, et al., incorporated by reference herein in its entirety. In the best mode, the pump of U.S. provisional patent application No. 61/015,731, to Danley, filed Dec. 21, 2007, which is incorporated by reference herein in its entirety and attached herewith as Appendix A. is used to supply liquid nitrogen. In one configuration of the present invention, using a measuring assembly having a mass of about 25 g, maximum sample heating rates in the range of 2000-3000° C./min can be achieved.

As shown in FIG. 1a, infrared furnace assembly 59 comprises reflector body 60, top plate 61, bottom plate 62, four lamps 26 and eight lamp holders 27. Reflector body 60 contains a cavity comprising intersecting portions of quadric cylinders. In one embodiment of the present invention, the intersecting quadric cylinder portions comprise portions of four parallel vertically oriented intersecting elliptical cylinders in which a lamp is situated at one focus of each of the four elliptical cylinders. The other foci of the elliptical cylinders are collinear and located at the center of the reflector body coincident with the central axis of the measuring assembly. The lamps may be 250 watt lamps having a T-3 configuration with an RSC (recessed single contact) base and 1¼" lighted filament length, thus delivering 1000 watts total power. The cavity of the reflector is polished and includes a coating that has very high infrared reflectivity, which is defined as having a hemispherical total reflectivity of at least about 0.95 in the near infrared electromagnetic spectrum up to 12 μm wavelength. One such suitable coating is Laser Gold, a proprietary electroplated coating produced by Epner Technology Inc. of Brooklyn, N.Y. Reflector top plate 61 is flat and has mounting lugs (not shown) for four lamp holders 27 that hold and make electrical contact with the upper end of each lamp. Surface 63 of the plate facing the cavity of the reflector block is polished and has a coating applied that has very high infrared reflectivity. In this configuration, hole 64 extends through the plate 61 allowing access to the measuring assembly for loading and unloading samples. Reflector bottom plate 62 is flat and has mounting lugs for four lamp holders that hold and make electrical contact with the lower end of each lamp. Surface 65 of the plate facing the cavity of the reflector block is polished and has a coating applied that has very high infrared reflectivity. In this configuration, hole 54 that extends through the plate allows heat sink extension 52 and thermal resistor 44 to enter the bottom plate and support the measuring assembly. Outer flat surface 85 of the bottom plate mates with flat surface 66 of the heat sink thus cooling the entire reflector assembly.

Figure 2:
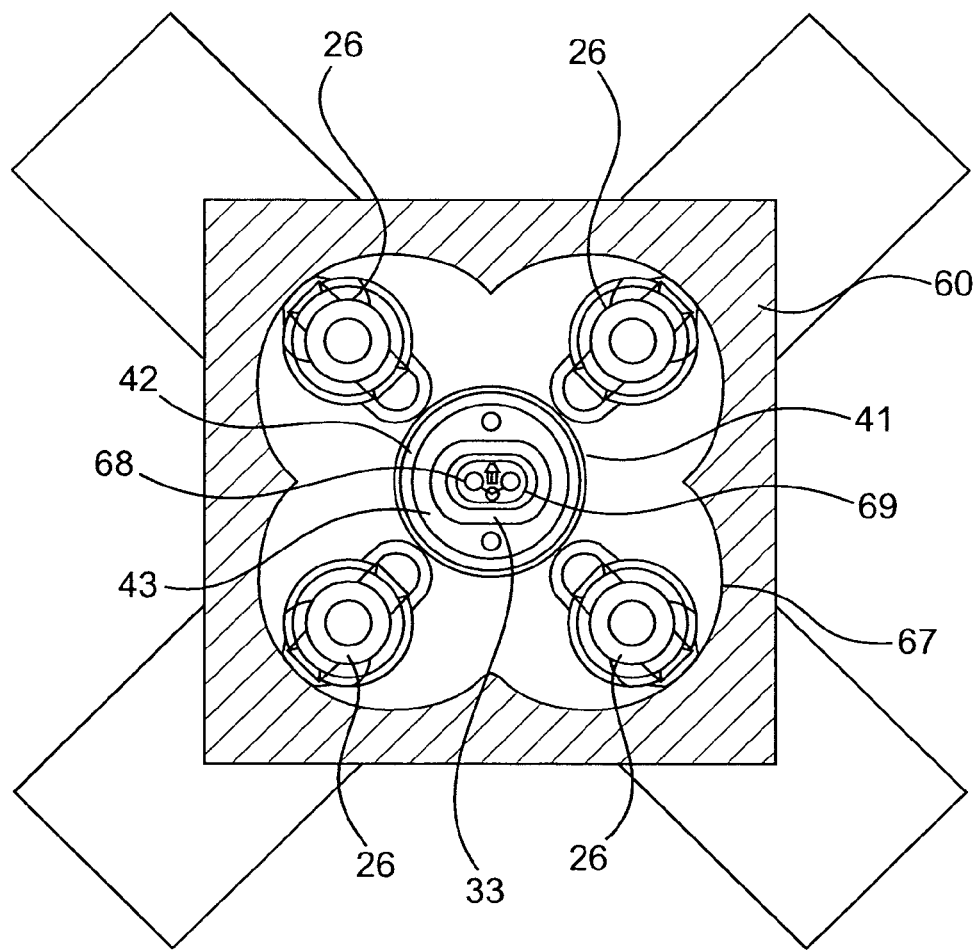

FIG. 2 shows a horizontal cross sectional view through the infrared furnace and measuring assemblies. In embodiments of the present invention, cavity 67 comprises a plurality of partial quadric cylindrical surfaces, where each partial quadric cylindrical surface is adjacent to one or more similar surfaces, as depicted in FIG. 2. The term "partial quadric cylindrical surface," as used herein, refers to a three dimensional surface that defines a partial cylinder whose cross sectional shape is that of a portion of a quadric curve, such as an ellipse. Thus, cavity 67 is defined by a series of four partial quadric cylinders that are each adjacent to two other partial quadric cylinders disposed on opposite sides of the cylinder in question.

In accordance with embodiments of the present invention, each partial quadric cylinder, such as a partial elliptical or parabolic cylinder, has a focus (which corresponds to a point in a plane of the partial quadric cylinder as viewed in cross-section, such as that depicted in FIG. 2) that corresponds to a position of a lamp 26.

In accordance with one embodiment of the present invention, cavity 67 of reflector body 60 comprises four intersecting partial elliptical cylindrical surfaces. Preferably, the four partial elliptical cylindrical surfaces each define a part of a respective elliptical cylinder (whose remaining portion is imaginary) that is arranged such that one focus of each elliptical cylinder is located equally spaced on a circle centered on the measuring assembly 41. The axis of each lamp 26 is centered on a respective focus of the equally spaced foci. The second focus of each elliptical cylinder is coincident with each other second focus and the centerline of the measuring assembly 41. Sensor 43 is located symmetrically with respect to the centerline of the measuring assembly within cavity 33 of the enclosure 42 having a sample position 68 and a reference position 69. Referring again to FIG. 1a, the cavity 67 of the reflector block 60 is designed to be approximately the same length (for the purposes of this disclosure, use of the phrase "approximately the same length" or "approximately equal" means that the ratio of length of reflector block cavity 67 and enclosure 42 along its axis is about 0.8-1.2 and aligned with conductive enclosure 42, such that enclosure 42 is surrounded by the reflector block cavity 67 over its entire length. In order to heat enclosure 42 efficiently, reflector block cavity 67 is designed not to extend substantially beyond the length of enclosure 42.

Figure 3:
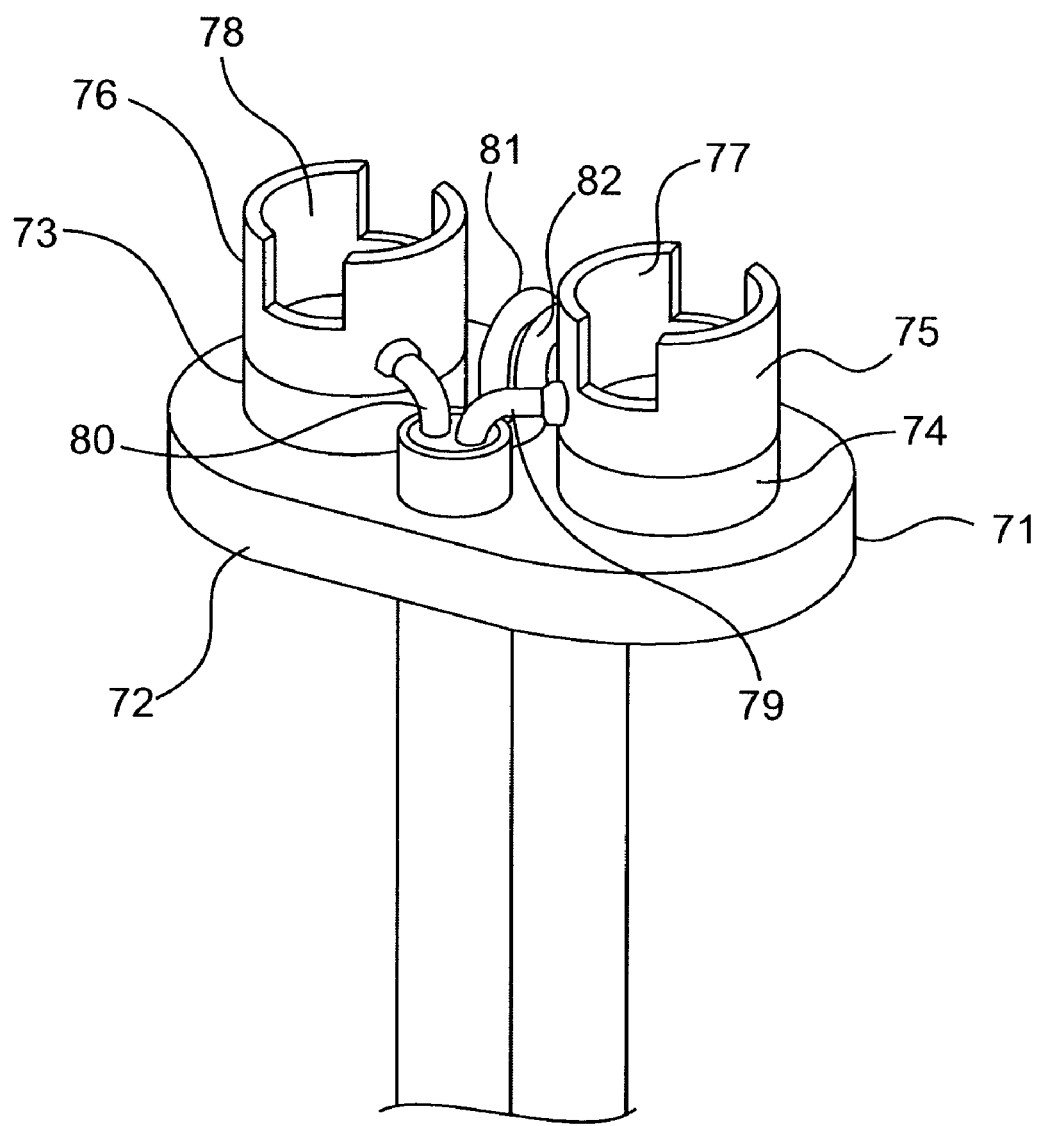
FIG. 3 shows details of a sensor assembly, according an embodiment of the present invention.

FIG. 3 shows details of sensor assembly 43, according to an embodiment of the present invention. Preferably, the sensor is constructed in accordance with that described in U.S. Pat. No. 6,431,747 and U.S. patent application Ser. No. 11/843,225, filed Aug. 22, 2007, and the heat flow rate measurement method taught therein may be practiced using the current invention. In one configuration of the present invention, the sensor base is made of a first material (such as a metal or alloy) constituting one member of a thermocouple pair and includes a relatively thicker (e.g. 0.5 mm to 1.0 mm thick) base 71 with a flat mounting surface 72 by which the sensor is mounted in the high thermal conductivity enclosure, and a pair of relatively thinner (e.g. 0.127 mm thick) wall cylindrical tubes 73 and 74 that form the measuring thermal resistances. In a preferred embodiment, the base 71 (as well as thin-walled cylinders 73 and 74) is made of constantan, the negative element of a type E thermocouple. A sample holder 75 and a reference holder 76 are made of a second, different material from that used to form base 71, such that holders 75 and 76 each form a thermocouple pair with the constantan (or other thermocouple material used to form base 71 and tubes 73, 74). Sample holder 75 includes a cavity 77 into which a sample contained in a sample capsule (not shown) can be inserted; reference holder 76 includes a cavity 78 into which a reference capsule (also not shown) containing a reference (if used) can be inserted.

In a preferred embodiment, the sample holders 75, 76 are made of chromel, the positive element of a type E thermocouple. A signal wire 79 that is made from the same alloy as used in the sample holder is welded to the sample holder and a signal wire 80 that is made from the same alloy as the reference holder is welded to the reference holder. A thermocouple comprising a wire 81 made from the same alloy as the base 71 and a wire 82 made from the same alloy as the sample and reference holders, is welded to the base. A thermocouple junction is formed at the interface between the upper ends of thin-walled tubes 73 and 74 and the bases of sample and reference holders 75 and 76. The sample and reference holders may be joined to the thin-walled tubes using welding, brazing or diffusion welding (also known as diffusion bonding) as described in U.S. Patent Application No. 60/839,673, although the preferred method is diffusion welding. In one configuration of the present invention, the sample measuring assembly and enclosure comprise a mass of about 10-100 g, and in one preferred configuration, about 25 g. In one configuration of the present invention, holders 75, 76 are designed with a diameter and height so that the volume of cavities 77, 78 is on the order of about $10^{-3}$ to $10^{-2}$ cm,$^{-3}$ which corresponds to sample (reference) materials having a mass in the range of about several tens of a microgram to several milligrams, depending on sample density.

A differential temperature signal $\Delta T$ representing the temperature difference between the sample and reference holders is measured between wires 79 and 80. A second differential temperature signal $\Delta T_0$ representing the temperature difference between the sample holder and the sensor base is measured between wires 79 and 82. The temperature of the base $T_0$ is measured between wires 81 and 82 and the temperature of the sample holder $T_s$ is measured between wires 79 and 81.

Figure 4:
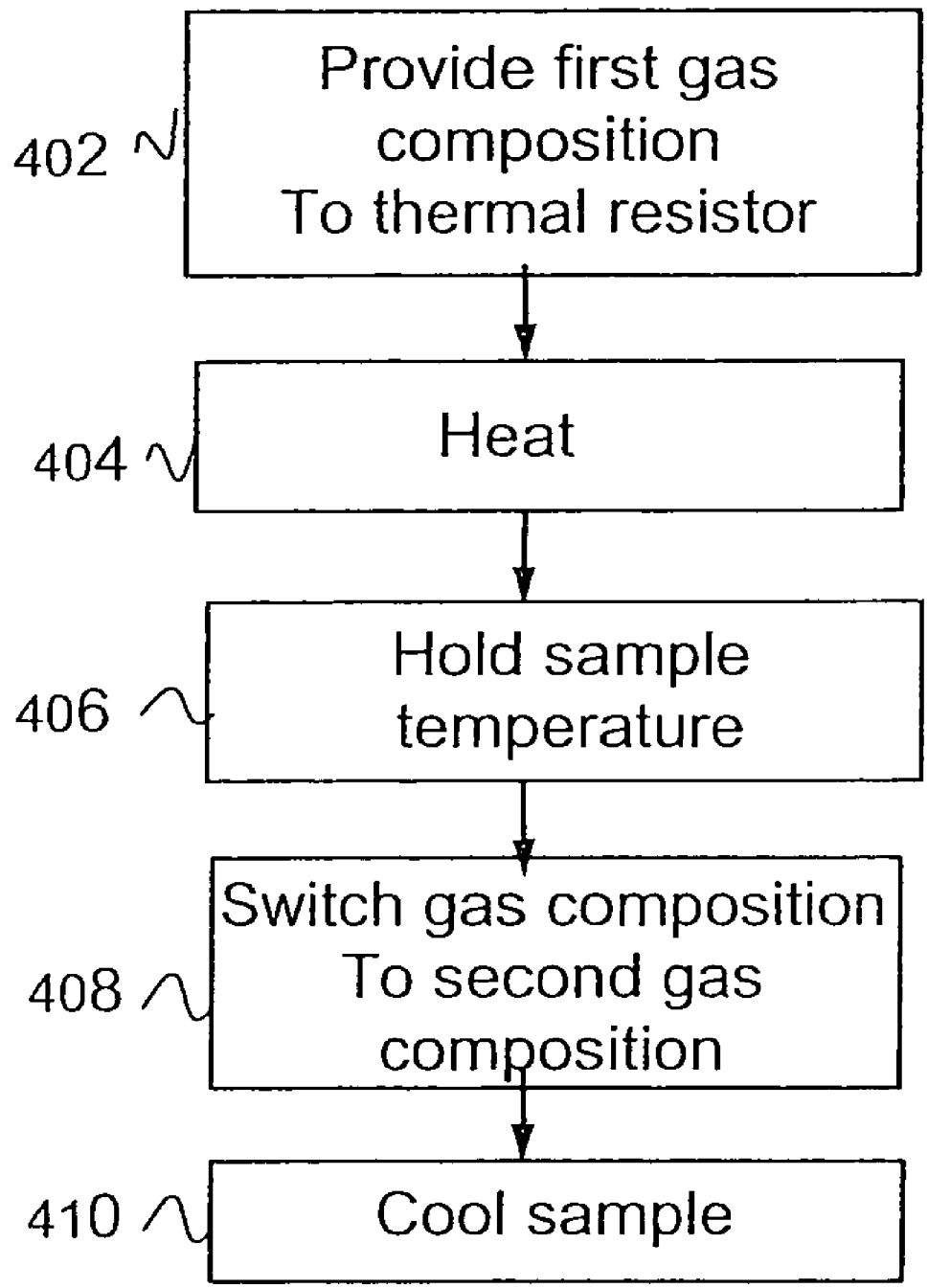
FIG. 4 illustrates exemplary steps involved in a method for thermal measurement using a variable thermal resistor, according to one embodiment of the present invention.

FIG. 4 illustrates exemplary steps involved in a method for thermal analysis using a variable thermal resistor, according to one embodiment of the present invention.

In step 402, a thermal resistor that comprises a gas-filled gap is supplied with a first gas composition. The thermal resistor forms part of a thermal analysis tool that includes a measurement enclosure coupled to a heat sink by the thermal resistor. For example, a low thermal conductivity gas like argon may be supplied to the gas-filled gap of the thermal resistor, in which case higher heating rates and lower cooling rates are achieved In step 404, the sample is heated. If the thermal resistor is provided with a low conductivity gas, such as argon or nitrogen, the relative sample heating rate can be increased. This is because the rate of sample heating depends on the rate at which heat is supplied to the sample and the rate at which heat leaves the sample. As the enclosure 42 absorbs heat emitted from the lamp assembly 59, enclosure 42 conducts heat to sensor assembly 43, which, during heating, typically has a lower temperature than enclosure 42. In addition, heat is conducted away from enclosure 42 through resistor 44 to heat sink 52. If resistor 44 has a relatively higher thermal resistance, the rate of heat loss from sensor assembly 43 to heat sink 52 is relatively lower. Accordingly, for a given rate of heat input from lamp assembly 59, the net heating rate of assembly 43 is higher.

In step 406, the sample temperature is held at steady state. The relative power supplied from heating lamps is adjusted such that the heat flow into the enclosure from the lamps is just offset by the heat flow out to the heat sink thus maintaining a constant temperature.

In step 408, the gas composition of the thermal resistor is switched to a second composition. In one embodiment of the present invention, the gas composition switching takes place while the sample temperature is maintained at a constant value. The switching of gas composition could take place, for example, during a planned isothermal hold step.

In step 410, the sample is cooled. If the second composition comprises a high conductivity gas, such as helium, the relative cooling rate is increased for a sample at an elevated temperature, because the rate of heat conduction to the heat sink is greater. Accordingly, both the sample heating rate and sample cooling rate can be independently maximized by appropriate choice of gas composition in the exemplary steps of FIG. 4.

The ability to independently maximize both sample heating and cooling rate affords better performance in measurement systems such as differential scanning calorimeters. In a DSC experiment, the temperature program is executed under closed loop control, such that heating segments and (occasionally) cooling segments of the experiment are performed at constant rates. Thus, in a DSC-type experiment, power is adjusted to maintain a programmed heating rate and possibly also a similar procedure is applied during a cooling cycle. For a given DSC instrument, the maximum power that can be applied controllably in a closed loop experiment is limited. This limitation on maximum power can limit the ability to use closed loop control to heat samples rapidly. If a sample loses heat to the environment, for example, through a thermal resistor coupled to a heat sink, too rapidly during heating, the power needed to maintain a given heating rate may exceed the ability of the instrument to controllably heat the sample. In addition, although it may be possible to heat a sample controllably at a given rate in a low temperature range where the difference between the sample temperature and outside environment is small, at higher temperatures the rate of heat loss from the sample to the heat sink may be such that the maximum available power is insufficient to produce the desired heating rate or to maintain the desired heating rate in a controllable fashion. It is therefore desirable to have a larger thermal resistance to minimize heat loss from the sample during heating. Accordingly, use of a high thermal resistance gas-filled gap would enable the programmed heating rate to be maintained to a higher temperature. Conversely, less power would be required to maintain a given heating rate at a given temperature as compared to using a low resistance gas-filled gap. In contrast, when attempting to run very high heating rate experiments using a low thermal resistance gas, the furnace power could reach its maximum value before the programmed temperature limit was reached and the heating rate would fall off as the sample continued to heat.

Conversely when trying to run high cooling rate experiments using a high thermal resistance, the furnace power could reach zero before the target temperature was achieved and the cooling rate would drop off causing the sample take a longer time than desired to cool.

Figure 5:
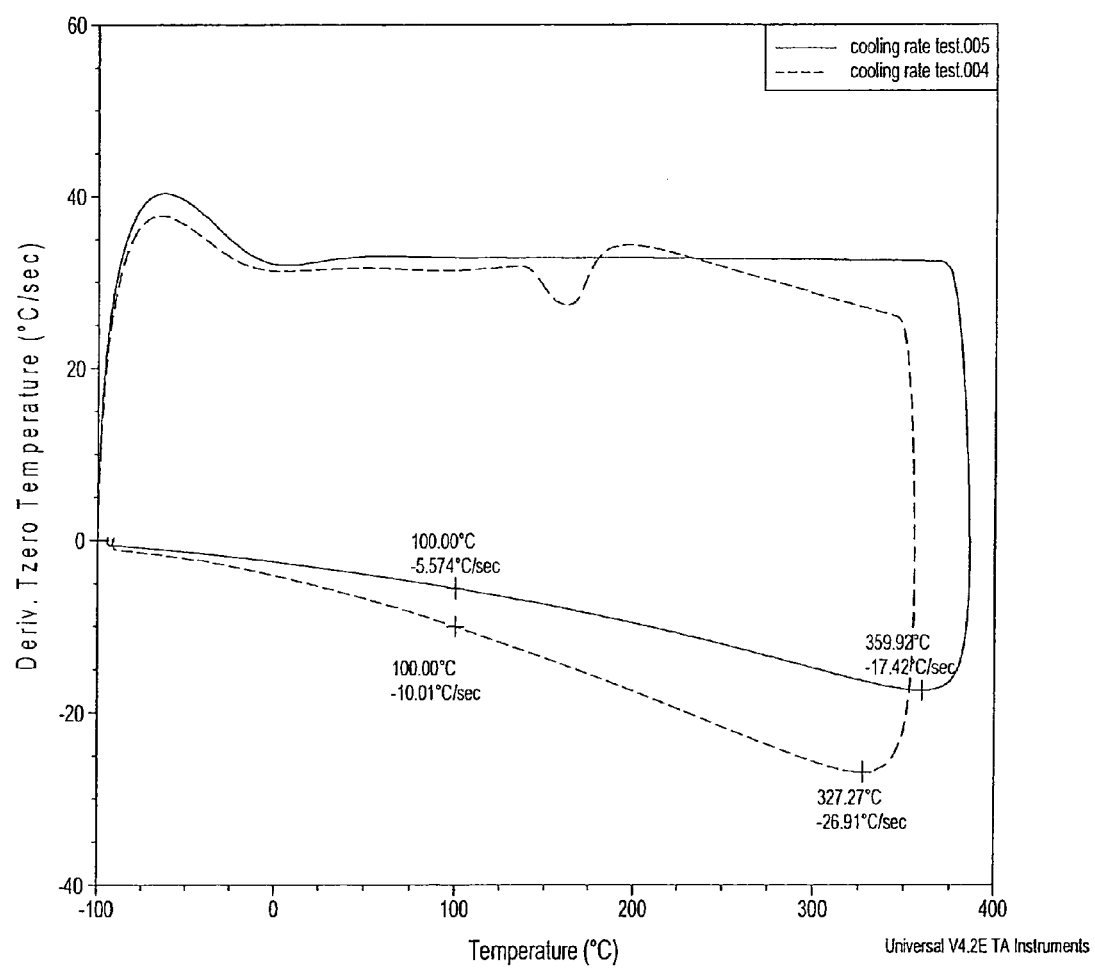
FIG. 5 shows the heating and cooling rates obtained under closed loop heating conditions when using an apparatus of the present invention having a configurable thermal resistance.

FIG. 5 shows experimental heating and cooling rates obtained under closed loop heating conditions when using an apparatus of the present invention having a configurable thermal resistance, that is, the thermal resistance can be modified to have different values. The plot shows two separate curves that correspond to the heating and cooling rates from two respective experiments superposed: the first experiment, "cooling rate test.004," was performed using helium, a high thermal conductivity gas, in the gap, resulting in a low thermal resistance; the second experiment, "cooling rate test.005," was performed using nitrogen, a low thermal conductivity gas in the gap, resulting in a high thermal resistance. In each experiment, the DSC was programmed to heat 33.33° C./sec (2000° C. min) to 400° C., after which it was allowed to cool ballistically, i.e. with no active temperature control. In the case of the experiment performed with a low thermal resistance, cooling rate test.004, the heating rate can only be maintained to 150° C., at which point the infrared furnace reaches maximum power and temperature control is lost and the heating rate cannot be maintained. Upon cooling, the maximum cooling rate achieved is −26.91° C./sec at 327.27° C. and at 100° C., the DSC is cooling at −10.01° C./sec. By comparison, the experiment performed using the high thermal resistance, cooling rate test.005, the programmed heating rate of 33.33° C./sec is maintained to 400° C. However, upon cooling, the maximum cooling rate achieved is −17.42° C./sec at 369.92° C. and at 100° C., the cooling rate is −5.574° C./sec.

As illustrated in FIG. 5, the use of low thermal conductivity (TC) gas in the thermal resistor enables a higher constant heating rate to be maintained to higher temperatures under closed loop control. However, the use of the low TC gas in the thermal resistor also results in a slower cooling rate. The use of a high TC gas in the thermal resistor results in a lower maximum temperature that can be achieved at high heating rate under closed loop control, but a higher cooling rate is also achieved.

Referring again to FIG. 5, in accordance with embodiments of the present invention, heating/cooling behavior can be modified by using different gases in a gas-filled gap variable thermal resistor to adjust experimental conditions as needed. For example, the data illustrate that for an experiment whose maximum temperature is less than about 125° C., stable heating rates of 33.3° C. are achievable using helium. Thus, for convenience, helium could be used for both heating and cooling cycles for experiments in which the maximum temperature does not exceed 125° C. and a heating rate of 33.3° C. or less is desired.

The ability to achieve both rapid heating rates and rapid cooling rates facilitates sample property measurements that are difficult to make using conventional thermal measurement apparatus. For example, for measurement at elevated temperature of properties of a partially crystalline or non-crystalline sample, it is desirable to heat rapidly to a desired temperature or temperature range. Rapid heating avoids recrystallization of the sample that could occur at intermediate temperatures during heating at a lower rate. This is because a substance that exists in partially crystalline or non-crystalline form typically exists in a metastable state having a higher free energy than a crystalline state of that same substance. During relatively slower heating, the substance (sample) may reach a temperature sufficient to overcome the energy barrier to recrystallization, at which point the sample begins to recrystallize to achieve a lower free energy (more stable) state. Subsequently, at higher temperatures, the recrystallized (stable crystalline) sample might melt, for example. Accordingly, if the object of experimental study were to determine the melting characteristics of the partially crystalline or non-crystalline form of the substance, the purpose would be defeated using a slow sample heating rate apparatus, because the sample would recrystallize before it reached a melting temperature. Similarly, the ability to vary the sample cooling rate and achieve high cooling rates facilitates "freezing in" of the sample structure at high temperature (by rapid cooling), as well as the ability to study the effect of sample cooling rate on transitions that occur within the sample during cooling.

Thermal measurement apparatus constructed according to embodiments of the present invention allow experiments to be conducted using the higher heating rates available with an apparatus having a high thermal resistance and the high cooling rates available with an apparatus having a low thermal resistance. More generally, the inherent tradeoff in fixed thermal resistance apparatus described above is eliminated. Because the sample heating and cooling rates can be varied independently of each other by providing a different thermal resistance at the sample heating stage as opposed to the sample cooling stage, both sample heating and sample cooling can be maximized in any given experiment.

It is to be further noted that the time required for switching from a low TC to high TC resistor (or vice versa) depends on the time needed to change the gas in the gap from the composition corresponding to the low TC resistor to the composition corresponding to the high TC resistor.

In one configuration of the present invention, the gas-filled gap is about 0.001" in the direction of predominant heat flow, meaning the shortest distance between the measuring assembly flat silver plate and the heat sink extension.

It should also be noted that the embodiments of the present invention disclosed above with respect to FIGS. 1-3 may be used to practice the inventions disclosed in U.S. Pat. Nos. 6,488,406, 6,561,692, 6,648,504, and 6,843,595, which disclose various configurations and components of apparatus related to differential scanning calorimetry.

In summary, in accordance with embodiments of the present invention, a thermal measurement apparatus capable of use as a heat flux DSC is configured to provide a combination of more rapid sample heating and cooling rates in comparison to conventional systems. Additionally, configurations of the present invention provide a more efficient arrangement for heating a DSC using an infrared heating system. Finally, more versatile sample measurements are provided by embodiments in which a heat flux DSC includes a variable thermal resistor. Thus, the thermal conductivity of the thermal resistor can be decreased during sample heating and increased during sample cooling, which allows the sample heating rate and sample cooling rate to be independently maximized during a single sample measurement.

FIGS. 6-9 below depict aspects of the present invention in which the components are configured to provide a continuous supply of cryogenic liquid to a heat exchanger when a pump is submerged within an unpressurized liquid. The terms "unpressurized liquid" or "liquid in an unpressurized state" refer to the fact that an excess pressure is not exerted upon a cryogenic liquid, for example, when the liquid is in a storage dewar, so that the pressure above the cryogenic liquid is similar to that of the atmosphere outside the dewar. Accordingly, as described in detail below, a bellows pump of the present invention is configured to operate to pump cryogenic liquid in a dewar that contains one or more vent portals communicating with the ambient atmosphere outside the dewar, such that at least one portal can remain open to the atmosphere to allow excess vapor to vent to the outside atmosphere during operation of the pump. The pressure in the dewar is therefore maintained at a level approximately that of the outside atmosphere.

Thus, unlike positive pressurized cryogenic cooling systems, no excess pressure above the cryogenic liquid is needed for the positive displacement pump of the present invention to operate so that vent portals need not remain sealed. This facilitates replenishing the dewar with cryogenic liquid without interrupting operation of the pump, since the pump can remain operational while submerged while refilling of liquid can take place through a connection to a source of liquid nitrogen, typically a bulk storage dewar.

Figure 6:
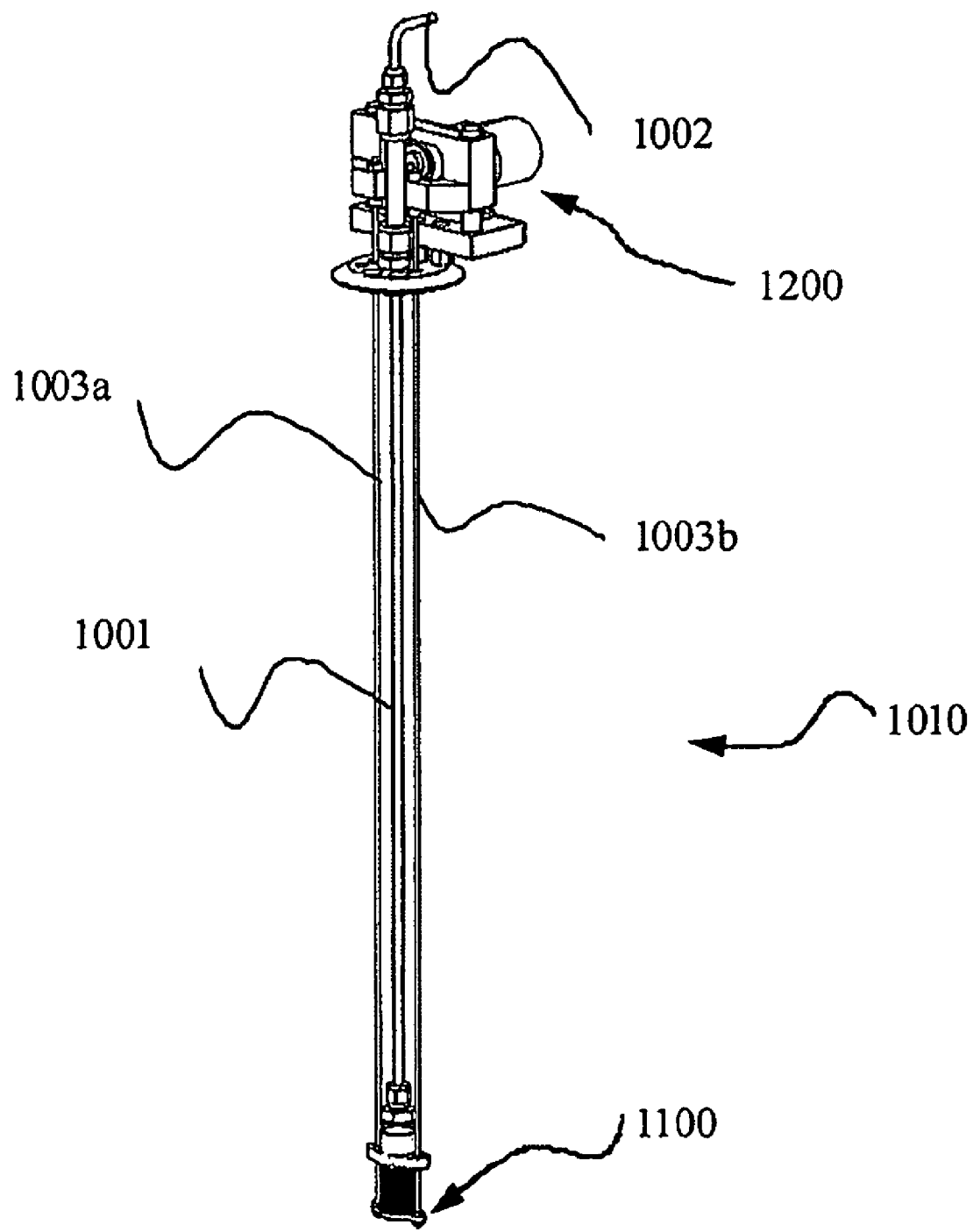
FIG. 6 shows an axonometric view of a liquid nitrogen pump assembly including a bellows pump assembly, drive assembly, drive rods and discharge tube, in accordance with an embodiment of the present invention.

In accordance with an embodiment of the present invention, FIG. 6 shows an overall view of a liquid nitrogen pump assembly comprising bellows pump assembly 1100, drive assembly 1200, discharge tube 1001 and drive rods 1003a and 1003b. Bellows pump assembly 1100 is connected to drive assembly 1200 by discharge tube 1001 through which liquid nitrogen can flow. Discharge tube 1001 has an end 1002 that is connected to a transfer line (not shown) that conducts liquid nitrogen to the apparatus to be cooled. Drive assembly 1200 supports bellows pump assembly 1100 via discharge tube 1001, which is made of a rigid material and serves to maintain a fixed separation between drive assembly 1200 and the top of pump assembly 1100. Drive rods 1003a and 1003b connect bellows pump assembly 1100 to drive assembly 1200 and impart the reciprocating motion of the drive assembly to the pump assembly.

Figure 7:
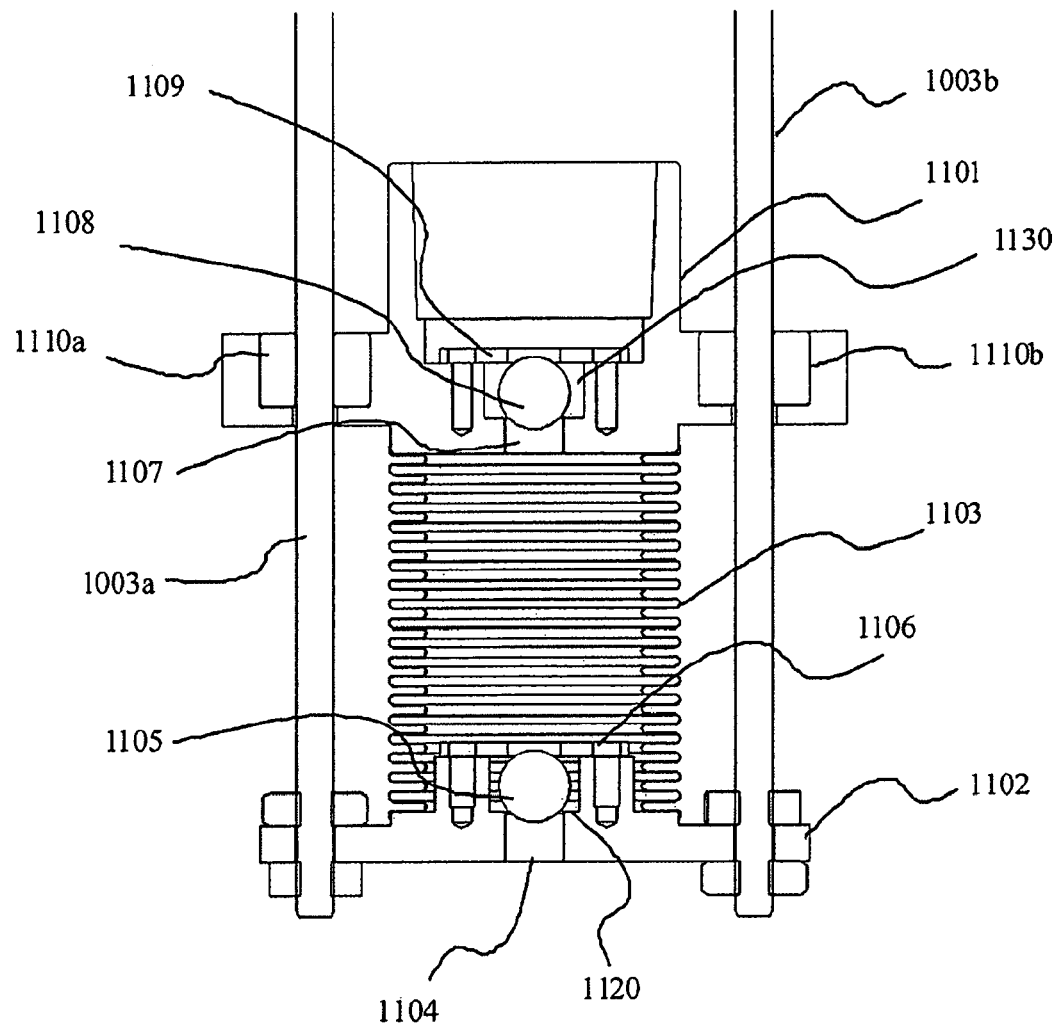
FIG. 7 shows a side view cross section of the bellows pump depicted in FIG. 6, in accordance with an embodiment of the present invention.

FIG. 7 is a vertical cross sectional view through bellows pump assembly 1100, showing details of its construction. The pump assembly comprises outlet head 1101, which contains a discharge port 1130, preferably configured as a discharge check valve assembly; inlet head 102, which contains an inlet port 1120 that is preferably configured as a suction check valve assembly; and bellows 1103. Outlet head 1101 is connected to bellows 1103, which, in turn, is connected to inlet head 1102. The connections between the bellows and outlet and inlet heads are made using a liquid tight method that prevents liquid from leaking. In an exemplary embodiment of the invention, the inlet and outlet heads are made from stainless steel, the bellows is made from electrodeposited nickel, and the bellows and inlet and outlet heads are joined together by soldering. However, in other embodiments of the present invention, the inlet and outlet heads, as well as the bellows can be made from other materials that do not become brittle at cryogenic temperatures and may be joined using methods other than soldering.

Outlet head 1101 is connected in a liquid tight manner to discharge tube 1001 (not shown in FIG. 7), which is configured to support the pump assembly 1100 (see FIG. 6) and hold it motionless during operation of the pump. Inlet head 1102 is connected to drive rods 1003a and 1003b, which move parallel to the axis of the pump and impart the reciprocating motion of the drive assembly to the inlet head, thereby alternately compressing and extending the bellows and causing the volume enclosed by the outlet and inlet heads and the bellows to alternately decrease and increase. As noted above, inlet head 1102 preferably includes a suction check valve 1120, which comprises inlet port 1104, check ball 1105, and check ball retainer 1106. The discharge port 1130 is preferably a discharge check valve assembly that comprises discharge port 1107, check ball 1108, and check ball retainer 1109.

As depicted in FIG. 7, bellows 1103 extends and compresses along a vertical axis. FIG. 7 depicts a position of the pump in which both check valves are closed, which occurs both at the point of maximum compression or maximum extension of the bellows 1103. Extension of the bellows causes liquid in the dewar (not shown) to enter the pump through suction port 1104, displacing check ball 1105 against the force of gravity; check ball retainer 1106 limits check ball motion so that during the compression stroke the check ball closes the suction port under the action of gravity and the tendency of liquid to flow backward through the suction port, thereby preventing liquid from flowing back out of the pump through suction port 1104. In a preferred embodiment of the present invention, suction check valve 1120 is configured as a very low pressure drop ball check valve. This denotes that very little pressure drop is required to cause the valve to open to permit cryogenic liquid to flow through it. By thus configuring the suction check valve 1120 to open with low pressure drop, the pressure drop on the cryogenic liquid is minimal during each pump cycle when liquid is drawn into the bellows.

The low pressure drop configuration using a ball check valve promotes improved operation of the pump within the cryogenic liquid because the tendency to form vapor in the liquid entering or leaving the pump is minimized. Cryogenic liquid in an unpressurized dewar has a temperature close to the boiling point of the liquid. Accordingly, slight increases in temperature inside the dewar tend to markedly increase vaporization. Similarly, significant pressure drops induced above the cryogenic liquid, such as those caused by a large pressure drop check valve, would induce a large increase in the rate of vaporization of the cryogenic liquid passing through the check valve. Thus, in accordance with the present invention, a low pressure drop check valve reduces the amount of vapor evolved during each cycle of the pump by minimizing the pressure drop experienced by the liquid flowing through the check valves.

Compression of the bellows forces liquid contained within the pump to leave the pump through discharge port 1107, displacing check ball 1108 against the force of gravity; check ball retainer 1109 limits check ball motion so that during the extension stroke check ball 1108 closes the discharge port 1107 under the action of gravity and the tendency of liquid to flow backward through the discharge port, thereby preventing liquid from flowing back into the pump. Drive rods 1003a and 1003b pass through guide bushings 1110a and 1110b that are installed in the outlet head. The bushings allow free motion of the drive rods but constrain them to move parallel to the axis of the bellows, thereby stabilizing the bellows.

Figure 8:
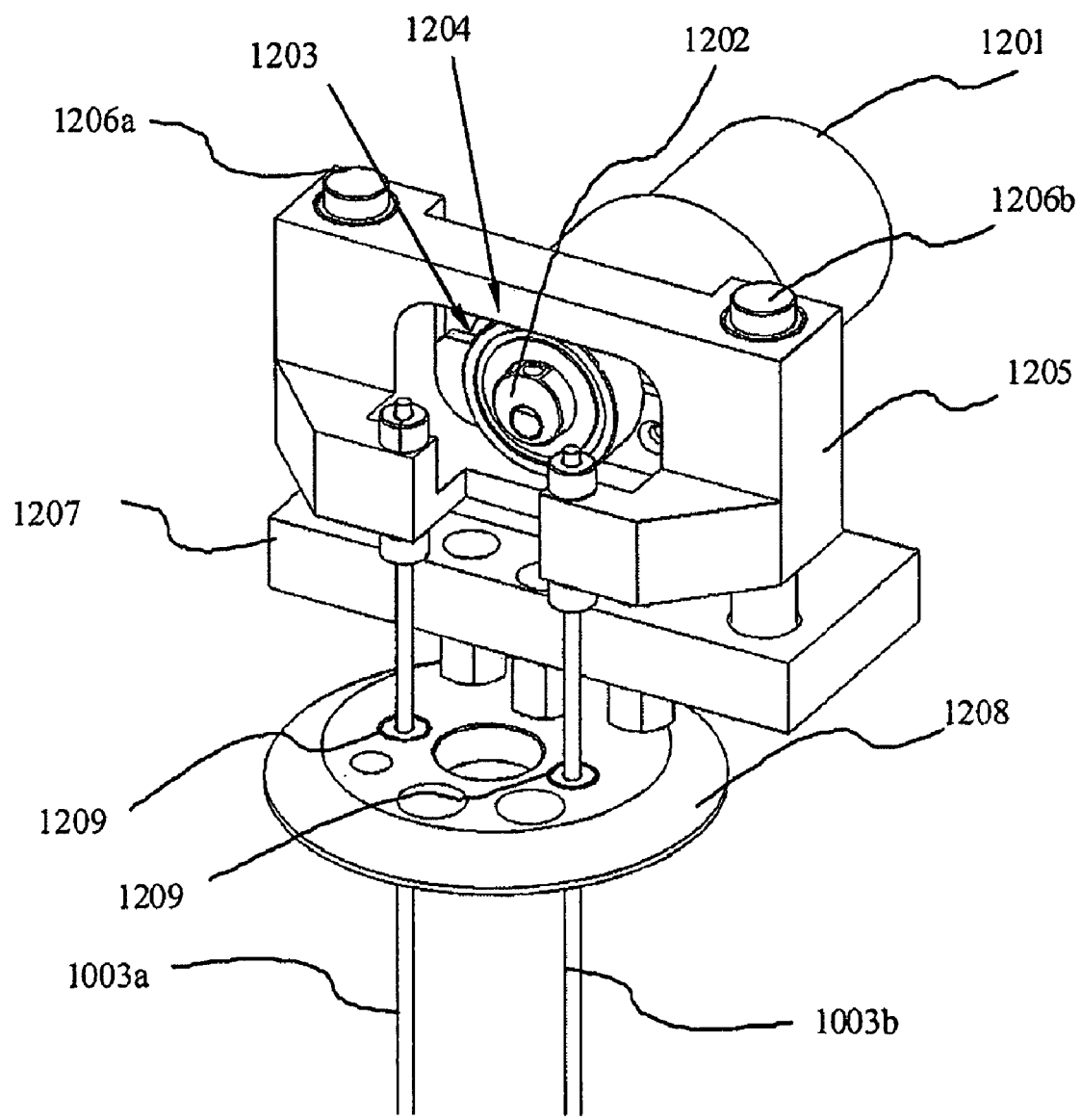
FIG. 8 shows an axonometric view of the drive assembly depicted in FIG. 6, according to an embodiment of the present invention.

FIG. 8 shows an axonometric view of drive assembly 1200. Gearmotor 1201 has an eccentric 1202 mounted on its output shaft; a ball bearing 1203 is mounted on the eccentric. The outer race of the ball bearing engages a slot 1204 in crosshead 1205 which is guided by a pair of shafts, 1206a and 1206b that constrain the crosshead to move parallel to the axes of the shafts, which are parallel to the axes of the pump and the drive rods. Shafts 206 and gearmotor 1201 are mounted on plate 1207. When the motor is energized, ball bearing 1203 rotates eccentrically on the gear motor output shaft, creating a reciprocating motion of the crosshead in a direction parallel to shafts 1206. Crosshead 1205 is fixedly attached to drive rods 1003a and 1003b, so that reciprocating motion of the crosshead imparts a reciprocating motion to the drive rods 1003a and 1003b and thereby to the pump. Mounting plate 1207 is attached to cover 1208, which is configured to clamp to the neck of a dewar containing the liquid. Drive rods 1003a and 1003b are configured to pass through cover 1208 and move freely in an up-and-down motion with respect to cover 1208. In one embodiment of the present invention, bushings 1209 installed in plate 1208 comprise a graphite material that facilitates smooth reciprocal motion of the drive rods 1003a, 1003b through cover 1208 over many pump cycles.

Thus, during operation of pump assembly 1010, drive system 1200 is located external to the dewar, while bellows pump assembly 1100 is immersed in the liquid in the dewar and is driven by system 1200 via rods 1003a and 1003b, which are free to move with respect to cover 1208.

In accordance with the present invention, the overall distance between plate 1208 and bellows pump assembly 1100 is tailored according to the size of the dewar to be used. In one embodiment of the present invention, separate liquid nitrogen pump assemblies 1010 can be provided, wherein in each assembly 1010, the lengths of drive rods 1003a, 1003b and discharge tube 1001 are configured to locate bellows pump assembly 1100 near the bottom of a dewar into which the bellows pump is to be immersed when cover 1208 is clamped to the top of the dewar. Accordingly, the lengths of drive rods 1003a, 1003b and discharge tube 1001 could be for example one foot for use with a small dewar, or could be several feet for use with a larger dewar, or any other suitable length.

Figure 9:
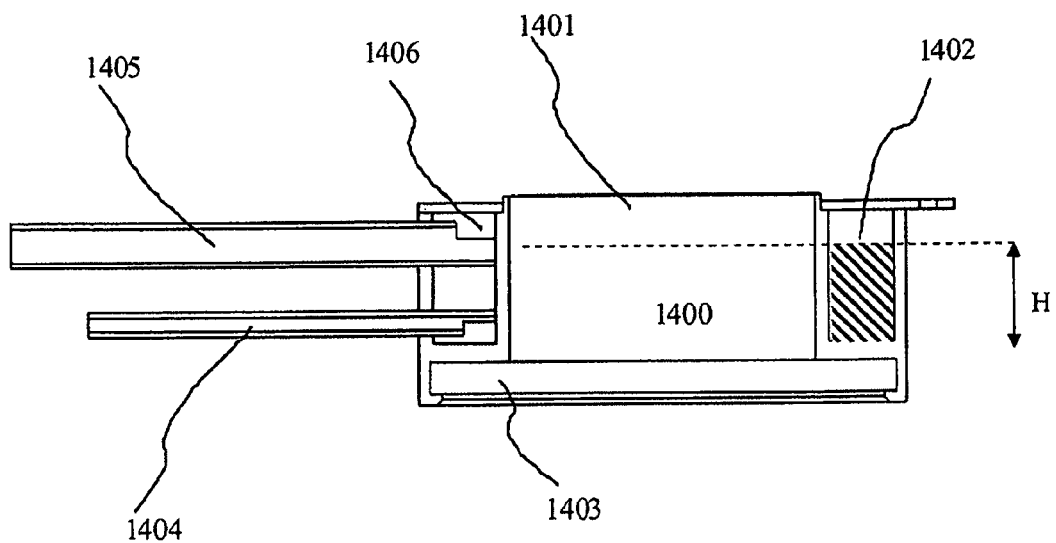
FIG. 9 shows a cross-section of a heat exchanger for a thermal analysis instrument that may be employed with the pump assembly of FIG. 6, according to another embodiment of the present invention.

FIG. 9 shows a cross sectional view through a heat exchanger 1400 that may be used to cool a thermal analysis or other instrument, in accordance with an exemplary embodiment of the present invention. The body 1401 of the heat exchanger is preferably in the form of a ring made of high thermal conductivity material, and contains an annular cavity 1402 to receive the coolant. The walls and the floor of the cavity comprise the heat exchange surface. In the exemplary embodiment shown, body 1401 comprises two parts (not shown), a first portion that includes the walls and floor of the annular cavity and a cover plate that is soldered to the first portion and which forms the top of the annular cavity. Heat exchanger 1400 incorporates a mounting surface 1403, by which it may be coupled to a thermal analysis apparatus, for example, to a sample stage of the apparatus. Liquid is supplied to the annular cavity 1402 by an inlet tube 1404 that discharges liquid into the annular cavity. Inlet tube 1404 is connected to end 1002 of the discharge tube of the pump by a suitable conduit (not shown). Preferably, vapor and excess liquid is discharged from the heat exchanger by exhaust tube 1405 that is connected to the dewar by a suitable conduit (not shown) to return the mixture of liquid and vapor to the dewar. The discharge tube is constructed with a weir 1406, over which liquid leaving the heat exchanger must flow, thereby regulating the level of liquid in the heat exchanger to be about the same height H or slightly higher than the top of the weir.

In the embodiment illustrated in FIG. 9, heat exchanger 1400 is in the form of a ring to accommodate a device coupled to heat exchanger 1400, such as the device disclosed in U.S. Pat. No. 6,523,998 to Danley, et. al. In accordance with embodiments of the present invention, the exact structure of the heat exchanger is tailored according to the thermal interface of the instrument to which it is coupled. Features common to any such heat exchanger include a cavity to contain the liquid having wetted heat exchange surfaces that are sufficiently large that adequate heat can be exchanged, a mounting surface to attach the heat exchanger to the instrument, and inlet and outlet connections to the heat exchanger. In other embodiments of the present invention, the heat exchanger can be an integral part of the instrument to be cooled, such that it is inseparable with the instrument.

In accordance with a preferred embodiment of the present invention, a pump system and heat exchanger, such as those described with respect to FIGS. 1-4 above, are configured to supply a continuous flow of cryogenic liquid to the heat exchanger that is sufficient to compensate for a maximum heat load applied to the heat exchanger. This denotes the fact that the continuous flow of cryogenic liquid is sufficient to remove heat from the heat exchanger by boiling heat transfer at a rate that is sufficient to prevent the critical heat flux point from being reached even under maximum heat load.

Advantageously, with the use of a positive displacement pump having low pressure drop suction and discharge check valves immersed in an unpressurized dewar, continuous flow of liquid can be supplied to a heat exchanger for any desired length of time, since the dewar can be refilled without stopping the pump. In accordance with embodiments of the present invention, in order to assure that the continuous cryogenic liquid flow is sufficient to prevent the critical heat flux point from being reached, the overall size and shape of the heat exchanger can be tailored according to the expected or measured heat load applied to a sample stage. For example, a heat exchanger can be configured such that the critical heat flux point is not reached so long as the exchanger remains full of liquid (say, up to the weir height). During an experiment, the positive displacement pump need thereby only operate to provide sufficient flow rate such that some liquid is continuously returned to the dewar, thus ensuring that liquid remains in the heat exchange cavity up to the height of the weir. This requires no active control system that may be complicated to operate, and allows for variations in flow rate, so long as the flow rate is sufficient to maintain some liquid return to the dewar at all times.

Thus, although the flow rate of cryogenic liquid through the heat exchanger may vary as the bellows pump cycles from an expanded state to a compressed state, in accordance with embodiments of the present invention, the stroke (back and forth distance traveled by the bellows) and diameter of the bellows, the diameter and length of lines conducting the cryogenic liquid, and the depth of the heat exchange cavity containing the liquid, among other factors, can be tailored to ensure that the heat exchange cavity remains full of liquid, such that liquid is returned to the dewar at all points of the pump cycle and under all heat flux conditions anticipated for the sample stage.

In accordance with an embodiment of the present invention, pump system 10 is also fitted with a system (not shown) to detect the level of liquid nitrogen in the storage dewar. One embodiment of the present invention comprises a liquid level detection system that contains a pair of self-heated thermal switches that close when immersed in liquid nitrogen and open when surrounded by vapor. One of the switches is mounted in the dewar at an elevation corresponding to the full level of liquid and closes to indicate that the dewar is full. The other switch is located at an elevation corresponding to the level at which the dewar should be refilled and opens to indicate that it should be refilled. The switches may simply provide a level indication for example by illuminating indicating lamps or may be used to operate a valve by which liquid may be automatically added to the dewar to refill it. Alternatively, a continuous level measuring system, such as a capacitive level detection (see Guy K. White, "Experimental Techniques in Low-Temperature Physics" 3ed, 1979, Oxford Science Publications, pp 50-54) system may be used. The capacitive level detection system may simply provide level indication via a meter or other suitable indicating device. Alternatively, the detection system may be used to supply a level indication to a logical circuit that actuates a valve by which liquid may be automatically added to the dewar when the liquid level falls to a preset value.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. For example, configurations of the present invention include a gap-type variable thermal resistor capable of supporting any combination of gases that exhibit a total gas pressure of from about one atmosphere to a vacuum, the latter condition providing for a lower thermal conductivity of the thermal resistor.

Notably, the scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A thermal measurement system, comprising:
   a measurement assembly for receiving a sample, the measurement assembly comprising an elongated cylinder;
   an infrared lamp assembly disposed circumferentially around the elongated circular cylinder and comprising an infrared reflector, wherein the infrared reflector includes a cavity having a length approximately the same as that of the elongated cylinder, and a bottom plate;
   a thermal resistor coupled to the measurement assembly and having a variable thermal resistance, the thermal resistor comprising:
      a gas-filled gap;
      a high thermal conductivity plate that is integral to the measurement assembly; and
      a heat sink surface disposed on a side of the gas-filled gap opposite to the high thermal conductivity plate;
   a heat sink thermally coupled to the thermal resistor and to the infrared lamp assembly, the heat sink comprising:
      an outer portion configured to abut against the bottom plate;
      a heat sink extension configured to extend through an opening in the bottom plate when the outer portion abuts against the bottom plate; and
   a seal assembly coupled to the measurement assembly,
   wherein the thermal resistor is operable to vary the thermal resistance between the measurement assembly and the heat sink during sample measurement, and
   wherein the seal assembly is operable to adjust a distance between the high thermal conductivity plate and the heat sink extension, so as to produce a gas-filled gap having a vertical height of less than a few tenths of a millimeter between the high conductivity plate and a top of the heat sink extension.

2. The system of claim 1, wherein the infrared lamp assembly comprises a plurality of elongated lamps arranged with their longitudinal axes parallel to an axis of the elongated cylinder and, wherein the infrared reflector comprises a plurality of partial quadratic cylindrical surfaces that each describe a portion of a cylindrical shape having a first focus coincident with a position of an elongated lamp.

3. The system of claim 1, wherein the gas-filled gap comprises an average vertical gap of between about 0.0001" and about 0.01."

4. The system of claim 1, further comprising one or more passages connected to the gas-filled gap and configured to supply gas to the gas-filled gap.

5. The system of claim 1, wherein the system is configured to produce a thermal resistance when the gas-filled gap comprises helium that is several times lower than a thermal resistance when the gas-filled gap comprises nitrogen.

6. The system of claim 1, wherein the system is configured to vary a gas composition of the gas-filled gap during sample measurement.

7. The system of claim 1, further comprising one or more thin spacers horizontally disposed in a spacer stack between the heat sink extension and high thermal conductivity plate, wherein the spacer stack is configured to produce a total average vertical gap having a dimension of about 0.0001" to 0.01" when a top and bottom of the spacer stack is brought into contact with the respective high thermal conductivity plate and heat sink extension.

8. The system of claim 1, wherein the elongated cylinder comprises silver.

9. The system of claim 1, wherein the thermal resistor is disposed substantially outside a region defined by the cavity of the infrared lamp assembly.

10. The system of claim 1, wherein the thermal resistor is configured to support a vacuum.

11. The system of claim 10, wherein the thermal resistor is configured to vary its thermal resistance by one or more of altering a total pressure within the gap from about atmospheric pressure to a vacuum and altering a composition of gas contained in the gap.

12. The system of claim 1, wherein the measurement assembly comprises a sensor assembly comprising a sample holder and reference holder.

13. The system of claim 12, wherein the sample holder and reference holder comprise hollow cylinders.

14. The system of claim 12, wherein a base portion of the sensor assembly comprises a first material of a thermocouple pair, and wherein the sample and reference holders each comprise a second material of the thermocouple pair.

15. The system of claim 12, wherein the measurement assembly comprises a mass of between about ten and one hundred grams.

16. The system of claim 12, wherein the sample holder and the reference holder each comprise a hollow cavity configured to receive respective sample and reference capsules.

17. The system of claim 16, wherein a volume of the sample and reference holder hollow cavities is between about 0.001 and 0.01 cubic centimeters.

18. A method for performing thermal analysis, comprising:
providing a variable thermal resistor between a sample measurement assembly and a heat sink in a thermal analysis tool;
heating a sample in the sample measurement assembly when the variable resistor has a first thermal resistance;
altering the variable resistor so that the variable resistor has a second thermal resistance different from the first thermal resistance; and
cooling the measurement sample while the variable resistor has the second thermal resistance,
wherein the variable thermal resistor comprises a gas-filled gap containing one or more thin spacers arranged horizontally in a spacer stack between the heat sink and the sample measurement assembly, and
wherein the one or more thin spacers are arranged to provide multiple gas layers between the heat sink and the sample measurement assembly.

19. The method of claim 18, wherein the one or more thin spacers comprise one or more thin metal sheets.

20. The method of claim 18, wherein the gas-filled gap is configured to receive gas through a passage connected to the gas-filled gap.

21. The method of claim 20, wherein the first thermal resistance is relatively higher than the second thermal resistance.

22. The method of claim 20, wherein the gas in the gas-filled gap comprises nitrogen during sample heating and helium during sample cooling.

23. The method of claim 20, wherein the spacer stack is configured to produce a total average vertical gap having a dimension of about 0.0001" to 0.01" when a top and bottom of the spacer stack is brought into contact with the sample measurement assembly and the heat sink.

24. A thermal measurement system, comprising:
a measurement assembly for receiving a sample, the measurement assembly comprising an elongated cylinder configured to receive heat from a heat source external to the elongated cylinder;
a thermal resistor coupled to the measurement assembly and having a variable thermal resistance; and
a heat sink thermally coupled to the thermal resistor, wherein the thermal resistor is operable to vary thermal resistance between the measurement assembly and the heat sink during sample measurement,
wherein the thermal resistor comprises a gas-filled gap containing one or more thin spacers arranged horizontally in a spacer stack between the heat sink and the measurement assembly, and
wherein the one or more thin spacers are arranged to provide multiple gas layers between the heat sink and the measurement assembly.

25. The thermal measurement system of claim 23, further comprising an infrared lamp assembly disposed circumferentially around the elongated cylinder and including a reflector cavity having a length approximately the same as that of the elongated cylinder, wherein the thermal resistor is disposed in a region outside of the elongated cylinder.

26. The system of claim 24, wherein the one or more thin spacers comprise one or more thin metal sheets.

27. The thermal measurement system of claim 24, wherein the thermal resistor is operable to change its thermal resistance.

28. The thermal measurement system of claim 27, wherein the thermal resistor further comprises:
a high thermal conductivity plate that is integral to the measurement assembly; and
a heat sink surface disposed on a side of the gap opposite to the high thermal conductivity plate,
wherein the spacer stack is configured to produce a total average vertical gap having a dimension of about 0.0001" to 0.01" when a top and bottom of the spacer stack is brought into contact with the respective high thermal conductivity plate and heat sink extension.

29. The thermal measurement system of claim 24, wherein the gas-filled gap is configured to receive gas from an external source.

30. The thermal measurement system of claim 29, wherein the gas-filled gap is configured to vary its thermal resistance when a composition of gas contained in the gas filled gap is changed.

31. A method of thermal analysis during rapid thermal processing, comprising:
providing a variable thermal resistor between a sample measurement assembly and a heat sink in a thermal analysis tool;
heating a sample in the sample measurement assembly when the variable resistor has a first thermal resistance; and
cooling the measurement sample while the variable resistor has a second thermal resistance less than the first thermal resistance,
wherein the variable thermal resistor comprises a gas-filled gap containing one or more thin spacers arranged horizontally in a spacer stack between the heat sink and the sample measurement assembly, and
wherein the one or more thin spacers are arranged to provide multiple gas layers between the heat sink and the sample measurement assembly, wherein the gas filled gap is configured to vary its thermal resistance when a composition of gas contained in the gap is changed.

32. The method of thermal analysis of claim 31, wherein the heating the sample comprises performing heating under closed loop conditions, wherein a constant heating rate is maintained.

33. The method of claim 31, wherein the one or more thin spacers comprise one or more thin metal sheets.

34. A method of thermal analysis during rapid thermal processing, comprising:
- providing a variable thermal resistor between a sample measurement assembly and a heat sink in a thermal analysis tool;
- heating a sample in the sample measurement assembly when the variable resistor has a first thermal resistance; and
- cooling the measurement sample while the variable resistor has a second thermal resistance less than the first thermal resistance,
- wherein the variable thermal resistor comprises a gas-filled gap containing one or more thin spacers arranged horizontally in a spacer stack between the heat sink and the sample measurement assembly, and
- wherein the one or more thin spacers are arranged to provide multiple gas layers between the heat sink and the sample measurement assembly,
- wherein the gas-filled gap is configured to receive gas from an external source,
- wherein the first thermal resistance corresponds to a condition in which the gap contains a low conductivity gas and the second thermal resistance corresponds to a condition in which the gap contains a high conductivity gas.

35. A method of thermal analysis during rapid thermal processing, comprising:
- providing a variable thermal resistor between a sample measurement assembly and a heat sink in a thermal analysis tool;
- heating a sample in the sample measurement assembly when the variable resistor has a first thermal resistance;
- cooling the measurement sample while the variable resistor has a second thermal resistance less than the first thermal resistance; and
- altering the variable resistor so that its thermal resistance changes from the first thermal resistance to the second thermal resistance while the sample is maintained at a constant temperature,
- wherein the variable thermal resistor comprises a gas-filled gap containing one or more thin spacers arranged horizontally in a spacer stack between the heat sink and the sample measurement assembly, and
- wherein the one or more thin spacers are arranged to provide multiple gas layers between the heat sink and the sample measurement assembly.

* * * * *